United States Patent [19]

Martin et al.

[11] Patent Number: 5,676,947
[45] Date of Patent: *Oct. 14, 1997

[54] METHOD FOR TREATING THROMBOEMBOLIC CONDITIONS USING THROMBOLYTICALLY ACTIVE PROTEINS

[75] Inventors: Ulrich Martin, Mannheim; Stephan Fischer, Polling, both of Germany

[73] Assignee: Boehringer Manneheim GmbH, Mannheim, Germany

[*] Notice: The portion of the term of this patent subsequent to Mar. 25, 2014, has been disclaimed.

[21] Appl. No.: 217,617

[22] Filed: Mar. 25, 1994

Related U.S. Application Data

[60] Continuation-in-part of Ser. No. 130,005, Sep. 30, 1993, abandoned, which is a division of Ser. No. 968,171, Oct. 29, 1992, abandoned, which is a continuation of Ser. No. 585,129, Sep. 28, 1990, Pat. No. 5,223,256, and a continuation of Ser. No. 165,577, Dec. 13, 1993, abandoned, which is a continuation of Ser. No. 892,629, Jun. 2, 1992, abandoned, which is a continuation of Ser. No. 527,498, May 23, 1990, abandoned.

[51] Int. Cl.$^6$ .............................. A61K 38/49; C12N 9/48; C12N 9/64

[52] U.S. Cl. .................... 424/94.63; 435/212; 435/226; 424/94.64

[58] Field of Search ................... 424/94.6, 94.3, 424/94.64; 435/212, 226; 514/12

[56] References Cited

FOREIGN PATENT DOCUMENTS 8804319  2/1988  Denmark.
302456   2/1988  European Pat. Off..

OTHER PUBLICATIONS

Collen, D. et al., *Blood* 71:216–219 (1988).
Saito, et al. *Ann. N.Y. Acad. Sci* 613:452–454.
Suzuki, et al. *Thromb. & Haemost.* 62(1):393 (1989).
Fu, K.P. et al. *Thrombosis Research* 50:33–41 (1988).

*Primary Examiner*—Dian C. Jacobson
*Attorney, Agent, or Firm*—Felfe & Lynch

[57] ABSTRACT

The use of various thrombolytically active proteins in therapy is disclosed. The proteins are markedly superior to wild type t-PA in their pharmacokinetic, pharmacodynamic, and safety profiles.

15 Claims, 6 Drawing Sheets

METHOD FOR TREATING THROMBOEMBOLIC CONDITIONS USING THROMBOLYTICALLY ACTIVE PROTEINS

RELATED APPLICATIONS

This application is a continuation-in-part of application Ser. No. 08/130,005 filed on Sep. 30, 1993, now abandoned, which is a divisional application of Ser. No. 07/968,171, filed on Oct. 29, 1992 and now abandoned, which is a continuation of Ser. No. 07/585,129 filed on Sep. 28, 1990, now U.S. Pat. No. 5,223,256, and U.S. patent application Ser. No. 165,577, filed Dec. 13, 1993, now abandoned, which is a continuation of Ser. No. 892,629 filed Jun. 2, 1992, abandoned, which is a continuation of Ser. No. 527,498 filed May 23, 1990 now abandoned. The patent and application are incorporated by reference in its entirety.

FIELD OF THE INVENTION

The present invention involves the use of thrombolytically active proteins useful in the treatment of subjects suffering from thromboembolic conditions.

BACKGROUND AND PRIOR ART

Coagulated blood contains polymeric fibrin which is the main component of the protein matrix. Fibrin is dissolved under physiological conditions by a fibrinolytic system in a reaction cascade which is similar to that of blood coagulation. The central reaction in this is the activation of plasminogen to plasmin which is for example mediated by the tissue-type plasminogen activator t-PA. Plasmin, in turn, dissolves fibrin which is the main component of the protein matrix of coagulated blood. The enzymatic activity of natural t-PA or t-PA obtained from eukaryotes by genetic engineering, i.e., the catalytic activation of plasminogen to plasmin, is very low in the absence of fibrin or fibrinogen cleavage products, but it can be increased more than 10 fold in the presence of these cleavage products.

T-PA is cleaved by proteases present in the blood into an A-chain and a B-chain, which remain bound to each other via a Cys—Cys bridge. The fact that t-PA can be stimulated to higher activities by, e.g., fibrin or fibrinogen cleavage products, is a significant advantage in comparison with other known plasminogen activators such as, urokinase and streptokinase (cf. for example M. Hoylaerts et al., J. Biol. Chem. 257 (1982), 212-2919; W. Nieuwenhuizen et al., Biochem. Biophys. Acta, 755 (1983), 531-533).

The mechanism of action of t-PA in vivo is described for example in Korniger and Collen, Thromb. Hamostatis 46 (1981), 561-565. The fact that the active site of this enzyme is on the surface of fibrin molecules would seem to make it a suitable agent for the treatment of pathological vascular occlusions such as myocardial infarcts. This has been confirmed, to a large extent, by clinical trials (Collen et al., Circulation 70 (1984), 1012: Circulation 73 (1986), 511).

A disadvantage of t-PA is its rapid clearance or low half life. Relatively large amounts of t-PA are necessary to achieve effective lysis of thrombi in view of this. High doses of this material lead to undesirable, harmful, and dangerous side effects, such as internal hemorrhaging.

A natural degradation product of t-PA is described in U.S. Pat. No. 4,970,159 which only contains the kringle II and protease domains, and whose N-terminus begins with alanine at position 160. (Hereafter, amino acid enumeration is by reference to that provided by Pennica et al., Nature 301: 214-221 (1983), incorporated by reference herein).

The clearance rate of the degradation product referred to supra does not differ significantly from that of wild type t-PA. Only chemical modification of the catalytic domain via attachment of a blocking group has been shown to improve this value.

U.S. Pat. No. 5,223,256, which is the grandparent of the subject application and is incorporated by reference herein, describes a non-glycosylated, thrombolytically active protein 355 amino acids in length, optionally extended at its N-terminus by a serine moiety. This protein has fibrin-dependent stimulatability comparable to wild type t-PA, but it was reported to lack the fibrin binding of this molecule. However, the thrombolytically active protein, referred to hereafter as "K2P", exhibited thrombolytic efficacy in vivo which was much improved compared to that of wild type t-PA. Also, when a dose is sufficient for an effective thrombolysis was administered, systemic fibrinolysis remained almost unaffected. This demonstrated that under physiological conditions, the described protein showed fibrin specificity. The protein described was shown to have very higher specific activity. Thrombolytically active proteins described therein had activities of 500 to 800 kU/mg.

The thrombolytically active protein of the '256 patent has been shown to be a protein which possesses the following properties:

(1) It has a half life which, on the average is about 4.5–5.0 times that of wild type t-PA ("wt-tPA" hereafter), with a range that is about 3.2–8.0 times that of wt-tPA. The mean half life of wt-tPA is 1.6–2.1 minutes. Enhanced half life is species dependent, as is discussed infra, but the ranges given are observed for all species tested.

(2) It has a clearance rate which is, on the average about 6.9–9.0 lower than that of wt-tPA (which has a clearance rate of from 22.2 to 41.6 ml/min/kg), and the clearance rate has a range of from 3.4 to 16.1 lower than wt-tPA. Again, this rate is species dependent.

(3) The "area under the curve" or "AUC" explained infra, for the molecule, is, on the average, about 8.0–9.5 times that of wt-tPA, at a range of from 3.5 to 17.5 times that of wt-tPA (which shows a mean AUC value of 84.1–133.3 IU/h/ml). Again, these values are species dependent.

These first three properties permit one to state that the thrombolytically active protein of the '256 patent, i.e., one which consists of amino acids 1–3 and 176–527 of wild type t-PA, has a pharmacokinetic profile which is about 4.5 to 9.5 greater than that of wild type t-PA.

(4) It induces 50% thrombolysis ($ED_{50}$), at doses about 4.0–11.5 times lower than wt-tPA, which has an $ED_{50}$ of 520,000–961,000 IU/kg, thus demonstrating 4.0–11.5 fold higher thrombolytic activity. Thrombolytically effective bolus doses are associated with reperfusion times which range from about 9 to about 44 minutes, average from about 15–31 minutes.

(5) It shows a better safety profile than that of wt-tPA, as, at thrombolytically effective bolus doses, the bleeding time is not prolonged more than about 2 times that of baseline, which is 2–3 minutes, as compared to wt-tPA.

(6) The levels of plasma fibrinogen, at thrombolytically effective bolus doses, is not reduced to levels below 25% of baseline, as compared to wt-tPA.

These properties are all inherent in the thrombolytically active protein of the '256 patent.

It has now been found that molecules which fulfill the foregoing criteria, i.e., which (a) have a pharmacokinetic profile which is 4.5 to 9.5 times greater than that of wild type t-PA (points 1–3); (b) have a pharmacokinetic profile 4.0–11.5 times that of wt-tPA (point 4), and (c) have a safety profile about twice that of wt-tPA (point 5) are useful as agents in the treatment of a thromboembolic conditions. The use of these molecules is the subject of the present invention, as is described in greater detail below.

EXAMPLE 1

The in vitro binding of the thrombolytically active protein of the '256 patent produced in *E. coli* to fibrin was determined according to the method described by Higgins and Vehar, Biochem. 26, 7786–7791 (1987) incorporated by reference.

Figure 1:
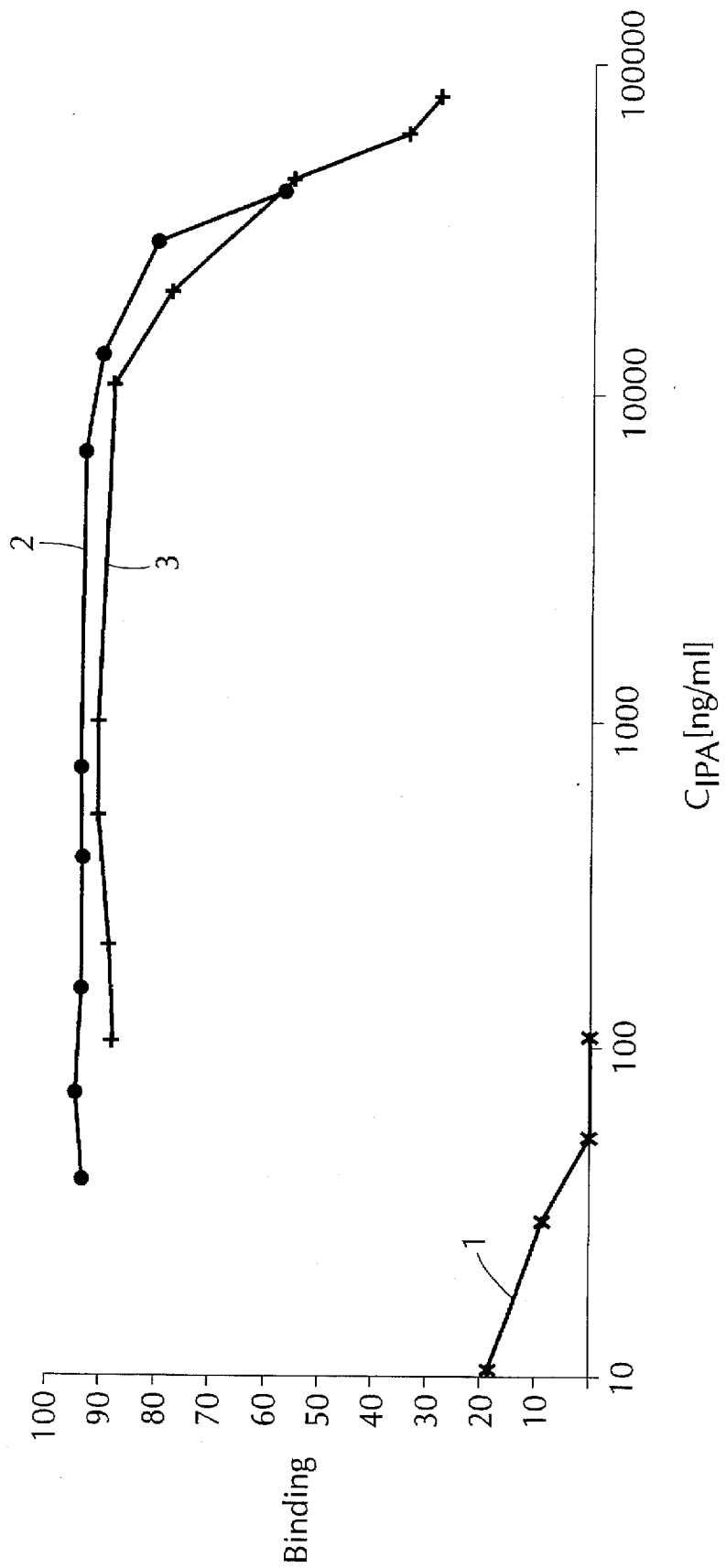
FIG. 1 shows a comparison of the fibrin binding of the thrombolytically active protein consisting of amino acids 1–3 and 176–527 of wt-tPA (curve 1) corresponding to the present invention with that of wt-tPA expressed in CHO cells (double stranded t-PA from CHO cells, cleaved at the physiological cleavage site Arg 257–Ile276, curve 2) and single stranded wt-tPA from CHO cells, (curve 3).
Figure 2:
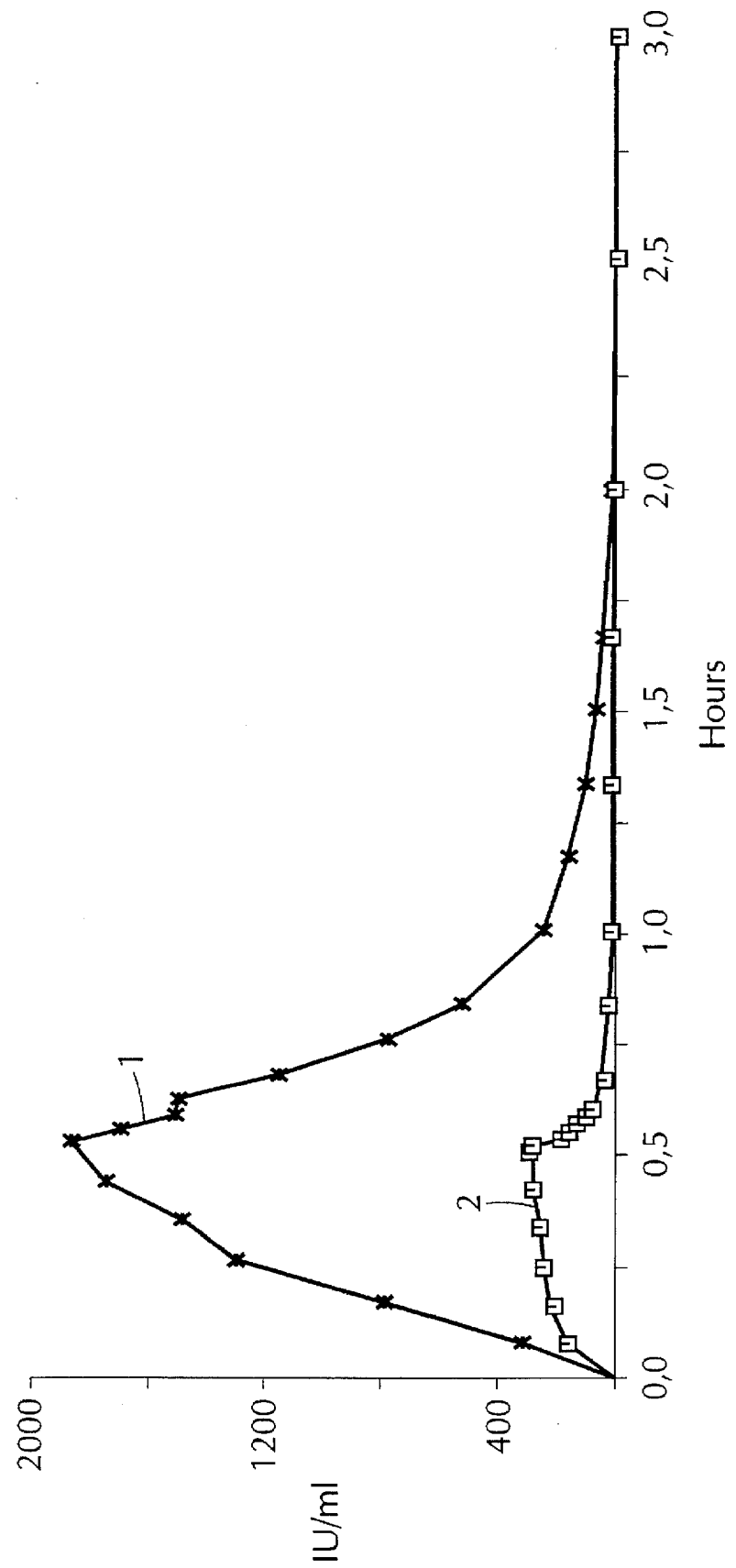
FIG. 2 and FIG. 3 show diagrams of the pharmacokinetics of t-PA activity of the protein of FIG. 1 compared to a commercially available wt-tPA preparation (Actilyse®); (curve 1: thrombolytically active protein: dose 200000 U/kg=0.25 mg/kg I.V. inf. for 30 min.; number of animals investigated (rabbits): 4; curve 2: wt-tPA; dose 200000 U/kg; I.V. inf. for 30 min., number of animals investigated (rabbits): 6).

FIG. 1 shows that the thrombolytically active protein compared to wt-tPA from CHO or wt-tPA from *E. coli*, showed no significant binding to fibrin.

EXAMPLE 2

The pharmacokinetic properties of the thrombolytically active protein of the '256 patent were compared to those of Actilyse®, in New Zealand white rabbits. Both fibrinolytic agents were infused for 30 minutes at a dose of 200000 IU/kg body weight. Plasma samples were taken at defined times before, during and after the infusion. Activity was measured with a spectrophotometric test according to J. H. Verheijen et al., (Thromb. Haemostas. 48, 266, 1982), modified according to H. Lill (z. ges. Inn. Med. 42, 478, 1987).

A calculation program for non-linear regression modified according to H. Y. Huang (Aero-Astronautics-Report 64, Rice University, 1–30, 1969) was used to calculate the pharmacokinetic parameters. The parameters were calculated individually using a bi-exponential pharmacokinetic model.

Figure 3:
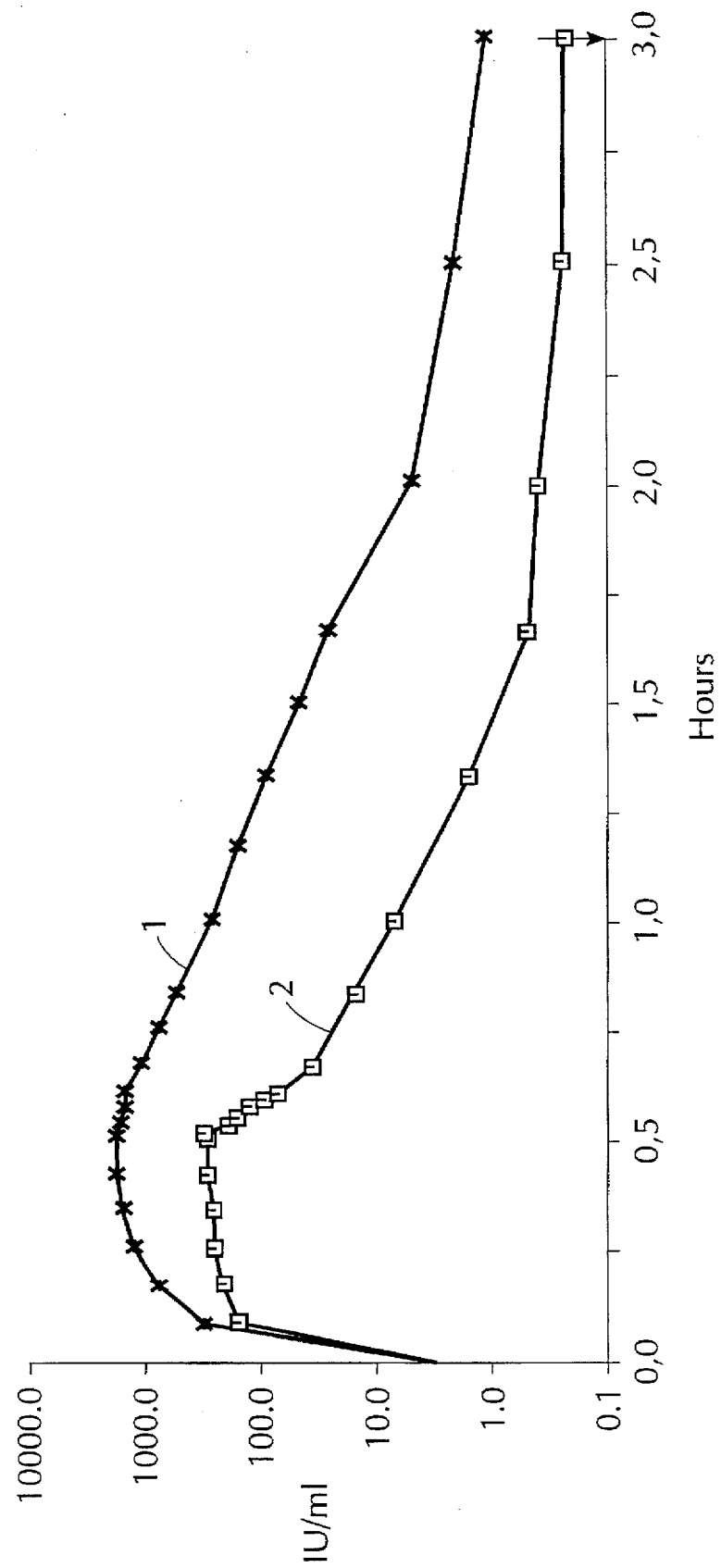

The thrombolytically active protein of the invention exhibits a five-fold longer half-life ($t1/2\alpha=10.3$ min, reduction of concentration in plasma) than Actilyse® (t-PA preparation of the Thomae company) (Table 1, FIG. 3). At the end of the infusion (after 30 min) with the protein, t-PA activity in plasma was measured as six-fold higher than that obtained with Actilyse®. The volume of distribution of the central compartment ($V_c$) was 46.8 ml/kg for the invention, compared to 73.7 ml/kg for Actilyse®. The total plasma clearance ($Cl_{tot}$) of the invention was reduced to 1.7 ($Cl_{tot}=3.2$ ml/min/kg) compared to Actilyse® ($Cl_{tot}=22.2$ ml/min/kg). When administering a fibrinolytic agent as a bolus injection "the area under the curve" (AUC) is of particular interest since it allows a comparison of the time-course of the prevailing plasma concentration. The invention shows an eight-fold higher AUC (1064 IU/ml×h) than Actilyse® (133.3 IU/ml×h).

The thrombolytically active protein of the invention showed, on the whole, a five- to eight-fold better pharmacokinetic profile at the same dose in comparison to Actilyse®.

EXAMPLE 3

Figure 4:
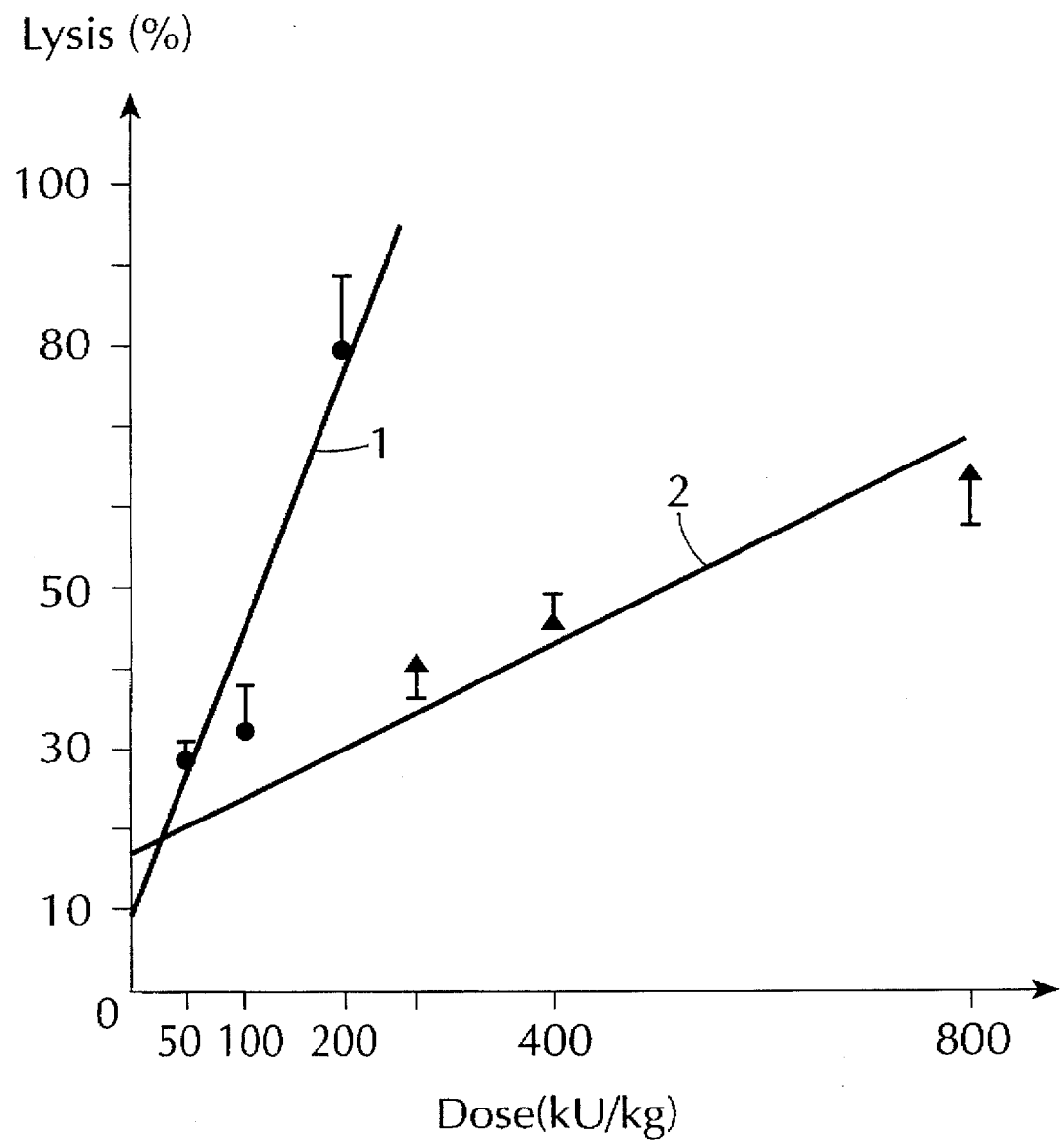
FIG. 4 shows dose-response curves (of rabbits) for thrombolysis for the protein mentioned in FIG. 1 in comparison with Actilyse® (shown is the mean value+SEM, 1 kU=1000 IU; curve 1: the inventive protein; curve 2: Actilyse®).

Pharmacodynamics of proteins in accordance with the invention were studied. To do so, the jugular vein model established by D. Collen et al., (J. Clin. Invest. 71, 368, 1983) was used to investigate the thrombolytic efficacy. The protein of the invention and Actilyse® were each examined at three dose levels. The fibrinolytic agents were infused for four hours and afterwards the rate of thrombolysis was determined (Table 2, FIG. 4).

With the aid of linear regression lines the dose of a 50% rate of thrombolysis ($ED_{50}$) was calculated to be 124000 IU/kg body weight for the invention, and 520000 IU/kg body weight for Actilyse. Thus four-fold higher thrombolytic activity than Actilyse is shown for the invention.

The inventive protein attained a dose-dependent plasma concentration of activity which, at a four-fold lower dose, was comparable with Actilyse®. A dose of 200 kU/kg body weight has thrombolytic activity comparable, to 800 kU Actilyse®/kg body and had slight effects on the coagulation parameters of fibrinogen, plasminogen and $\alpha_2$-antiplasmin. These do not differ from the effects of a dose of 800 kU Actilyse®/kg body weight.

This example shows that at a dose reduced to ¼th that of wt-tPA, protein in accordance with the invention do not differ in their effect on the coagulation system, or in plasminogenolytic activity in plasma.

TABLE 1

Pharmacokinetic parameters derived from computer calculations
of the t-PA plasma concentrations - time data based on t-PA-activity

| Agent (Dose: 200000 IU/kg bw) | $t_{1/2\alpha}$ (min) | $t_{1/2\beta}$ (min) | $C_{inf}$ (IU/ml) | $V_C$ (ml/kg) | $Cl_{tot}$ (ml/min/kg) | $AUC_{extrapol.}$ $\left(\frac{IU}{ml} \cdot h\right)$ |
|---|---|---|---|---|---|---|
| Invention (n = 4) | 10,3 ± 1,7 | 14,9 ± 4,6 | 1986,6 ± 762,6 | 46,8 ± 14,7 | 3,2 ± 1,1 | 1064,4 ± 443,2 |
| Actilyse ® (n = 6) | 2,1 ± 0,6 | 10,9 ± 2,4 | 326,6 ± 118,1 | 73,7 ± 19,7 | 22,2 ± 7,6 | 133,3 ± 44,1 |

TABLE 2

Thrombolysis, level of t-PA plasma activity (at the end of a 4 h infusion)
and haemostasis parameters (30 min after the end of the infusion) of Invention,
Actilyse ® and solvent

|  | Invention 200 kU/kg | Invention 100 kU/kg | Invention 50 kU/kg | Solvent NaCl/Tween | Actilyse ® 800 kU/kg | Actilyse ® 400 kU/kg |
|---|---|---|---|---|---|---|
| Thrombolysis (%) | 79 ± 9 (n = 3) | 32 ± 6 (n = 5) | 29 ± 1 (n = 2) | 11 ± 1 (n = 6) | 64 ± 6 (n = 7) | 46 ± 3 (n = 6) |
| Plasma t-PA activity (IU/ml) | 93,7 ± 18,2 | 44 ± 3 | 7 ± 0 | — | 107 ± 27 | 47 ± 9 |
| Fibrinogen (%) | 74 ± 2 | 90 ± 6 | 86,5 ± 6 | 92 ± 3 | 77 ± 6 | 90 ± 3 |
| Plasminogen (%) | 79 ± 7 | 75 ± 6 | 87 ± 11 | 98 ± 10 | 77 ± 4 | 88 ± 4 |
| $\alpha_2$-Antiplasmin (%) | 70 ± 1 | 70 ± 4 | 93 ± 4 | 98 ± 8 | 74 ± 6 | 87 ± 3 |

Mean ± SEM;
kU = 1000 IU;
Haemostasis-Parameter (% with reference to base line)

EXAMPLE 4

An experimental model for acute myocardial infarction in animals were chosen as an example in order to examine the thrombolytic effect of the proteins of the invention on arterial thrombi. The dog was chosen as the animal species. The method for the formation of a coronary artery thrombus was a modification of the technique of Romson et al., (Thromb. Res. 17, 841, 1980). In the open thorax of artificially respirated, anaesthetized dogs, the intimal surface of the ramus branch of the left circumflex coronary artery (LCX) was electrically stimulated (150 µA) and by this means a thrombus was produced. Previously, a screw had been applied distal to the thrombosis in order to eliminate a reactive hyperaemia by the experimental stenosis. Proximal to the coronary thrombosis the LCX was equipped with an electromagnetic flow measuring head in order to be able to measure the reperfusion.

In order to determine the most effective dose of the protein, four different doses of the thrombolytically active protein, and wt-tPA, and placebos were injected as an initial single intravenous bolus over 1 min into heparinized dogs; 6 animals were injected with each dose. Plasma samples were taken before and at defined times after the injection in order to determine the plasma concentration of the t-PA activity and of fibrinogen, plasminogen and $\alpha_2$-antiplasmin as well as the number of thrombocytes in whole blood. Fibrinogen was measured coagulometrically according to Clauss (Acta haemat. 17: 237, (1957)), incorporated by reference in its entirety.

Plasminogen and $\alpha_2$-antiplasmin were measured spectrophometrically as described by Collen et al., (J. Clin. Invest. 71, 368, 1983). In addition, the "Simplate bleeding time" was measured on the hind leg of the dogs using a lancet (Simplate® I, Organon Teknika, Eppelheim, FRG), during a venostatis of 40 mm Hg (J. Surg. Res. 27, 244, 1979). The statistical comparison of the measured values after injection with the control value before injection was carried out with the Wilcoxon Test for pair differences.

In order to describe the thrombolytic effect, the number of reperfused animals per dose-group (=reperfusion rate) as well as the time up to the reperfusion (=reperfusion time) was determined. In addition, the wet weight of the residual thrombus still present two hours after injection was measured and the number of animals with re-occlusion after reperfusion (=re-occlusion rate) was determined. With the aid of a semi-logarithmic regression analysis of the dose-effect (reperfusion rates) relationships, the effective dose for 50% reperfusion rate (=$ED_{50}$) was determined for each substance. The statistical comparison of the weights of the residual thrombi was carried out using the Wilcoxon-Mann-Whitney Test for unconnected random samples.

The plasma concentration of the t-PA activity was measured with a spectrophotometric test according to Verheijen et al., (Thromb. Haemost. 48, 266, 1982) modified according to Lill (Z. gesamte Inn. Med. 42, 478, 1987). A calculation program for non-linear regression modified according to H. Y. Huang (Aero-Astronautics-Report 64, Rice University, USA, 1–30, (169) was used to calculate the pharmacokinetic parameters. The parameters were calculated individually using a bi-exponential pharmacokinetic model after subtraction of the endogenous basal level of t-PA activity from the subsequent measured values.

The following results were obtained:

1. Pharmacodynamics in the Dog

The protein of the invention showed a dose-dependent reperfusion rate after intravenous injection. The maximum effect (reperfusion rate of 100%) was achieved after an injection of 200 kU/kg body weight. The dose which produced 100% success when wt-tPA was used, was 1600 kU/kg body weight. A comparison of the $ED_{50}$ values yielded an 11.5-fold lower value for the invention ($ED_{50}$=83 kU/body weight) as compared to Actilyse® ($ED_{50}$=961 kU/body weight). The administration of a placebo did not result in reperfusion. The weight of the residual thrombus in the placebo animals was 9.6±1.6 mg (mean±SEM); both protein showed a statistically significant reduction in the weight of the residual thrombus with increasing doses, as compared to the placebo control. Reperfusion occurred with both fibrinolytic agents, as an average over all animals, after 25.9±3.5 min for the invention or after 24.2±6.2 min wt-tPA. Most of the dogs treated with either agent reoccluded after reperfusion.

2. Pharmacokinetics in the Dog

After intravenous injection of 200 kU/kg of protein it was seen that the fast phase of decrease in the plasma concentration, expressed as $t_{1/2}\alpha$, was about 4.5 times longer with the thrombolytically active protein of the '256 patent at 7.2±1.1 as was wt-tPA at 1.6±0.2 min (Table 4). The plasma concentration of the '256 patent protein, determined immediately after the end of the injection was about twice as high as that of wt-tPA. The clearance of the protein from the plasma (plasma clearance=$Cl_{tot}$) was nine-fold slower than of Actilyse®. Correspondingly, the area under the plasma concentration-time curve of the protein approximately 9.5 times larger than that of wt-tPA.

3. Fibrin Specificity in the Dog

Two hours after injection of the thrombolytically active protein there was a dose-dependent, slight reduction in the residual concentration of fibrinogen to 81±10% at the highest dose (200 kU/kg body weight). In contrast, the fibrinogen concentration was almost completely reduced to 3±0% after administration of the highest dose of wt-tPA (1600 kU/body weight) (Tab. 5). If one carries out a semi-logarithmic regression analysis of the dose-side-effect (fibrinogen reduction) relationship and determines the residual concentration of fibrinogen which corresponds to the $ED_{50}$ for thrombolytic effect, it results that for equipotent doses the residual content of fibrinogen was 92.5% with the invention as compared to 38.6% with wt-tPA. There is also a dose-dependent lowering of the residual contents of plasminogen and $\alpha_2$-antiplasmin 2 hours after injection which is more pronounced with wt-tPA than with the invention. Only the concentration of platelets is virtually uninfluenced by the two substances.

4. Influence on the Bleeding Time in the Dog

Figure 5:
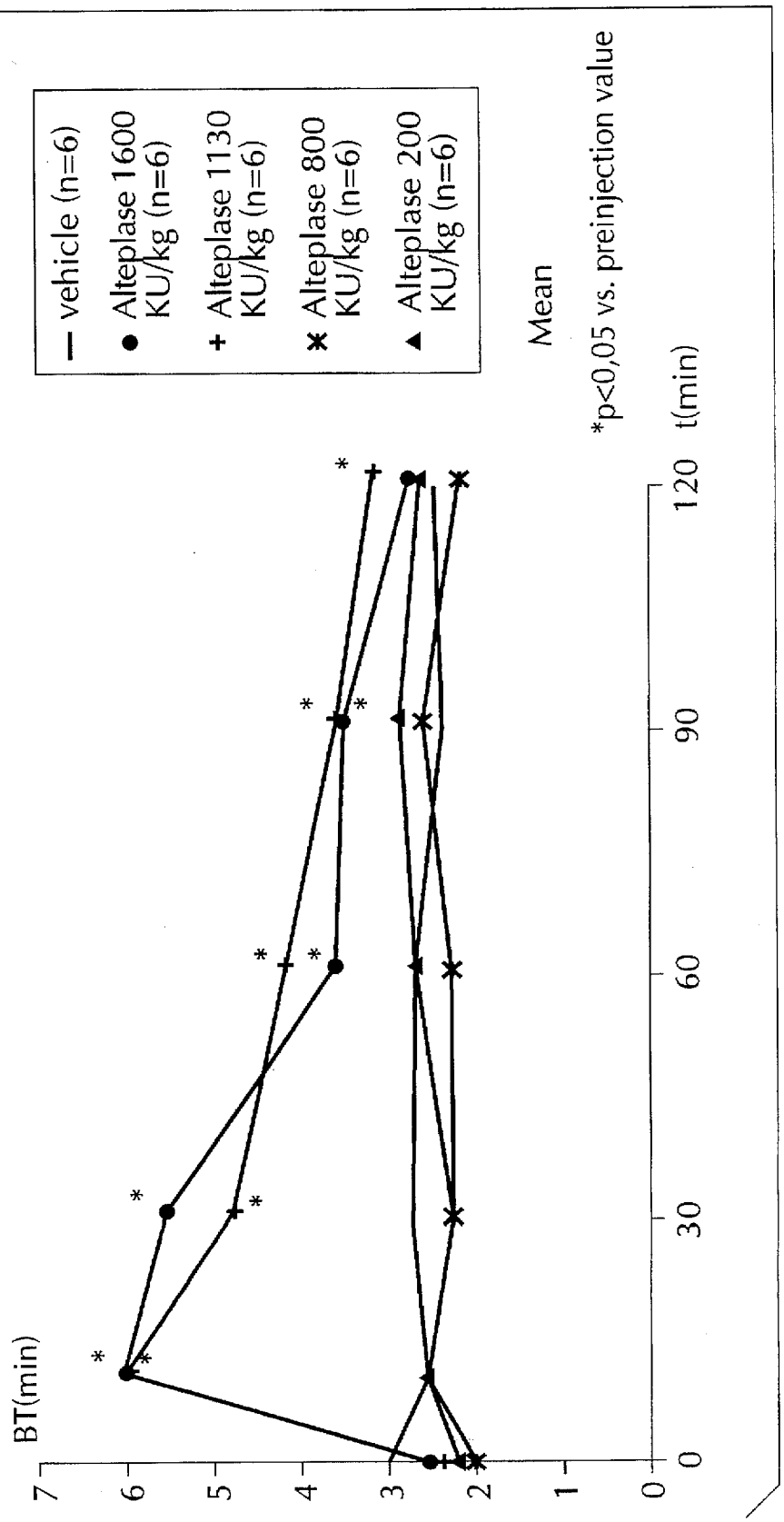
FIG. 5 shows the time course for Simplate bleeding time (BT) before and after an i.v. bolus injection of placebo or increasing doses of Actilyse® in anaesthetized dogs.
Figure 6:
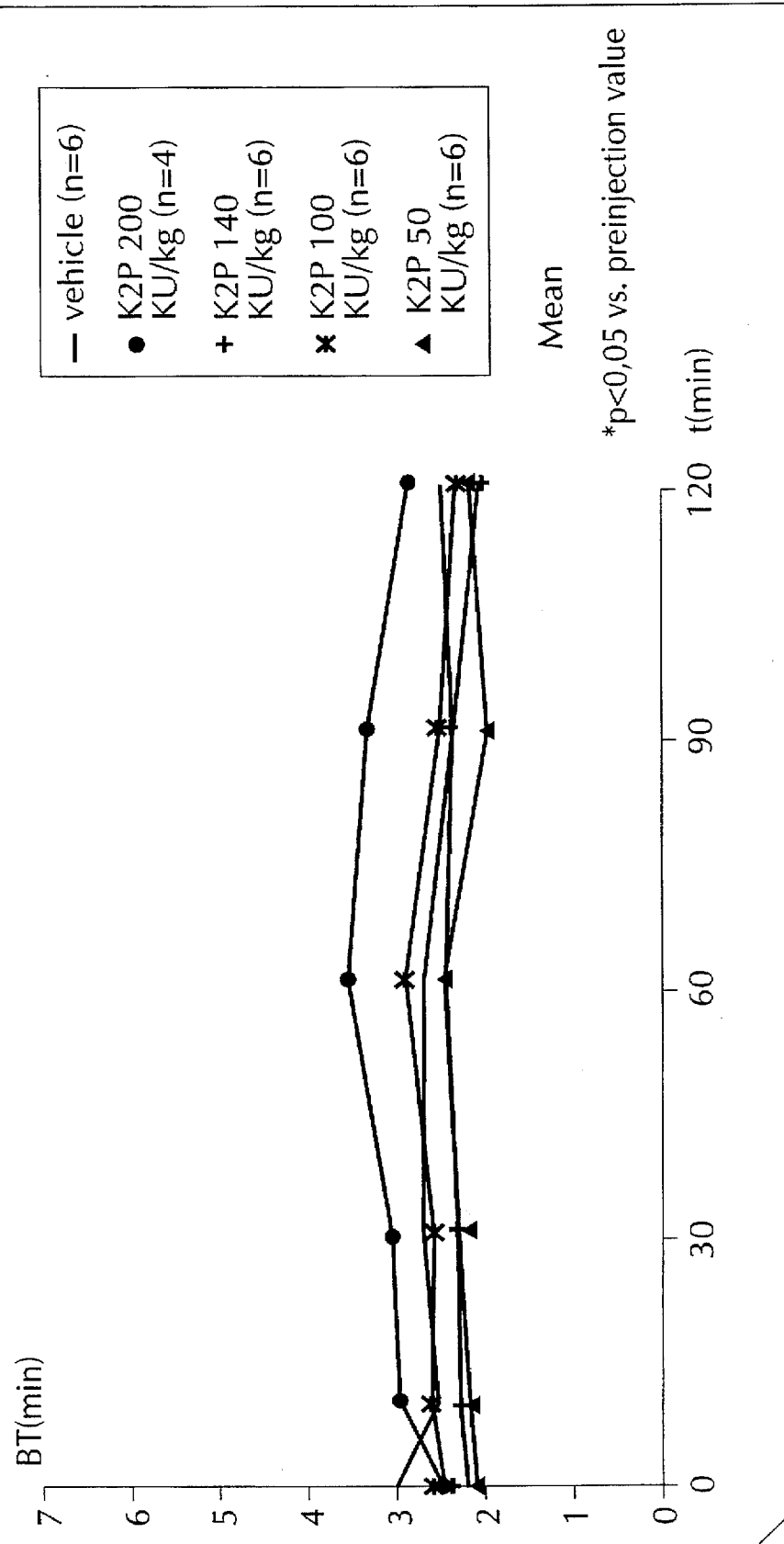
FIG. 6 shows the time course for Simplate bleeding time (BT) before and after an i.v. bolus injection of placebo or increasing doses of the thrombolytically active protein of FIG. 1.

The intravenous injection of the protein of the invention did not result in a statistically significant increase in the bleeding time in comparison with the control value before injection at all four doses investigated (FIG. 6). In contrast, wt-tPA increased the bleeding time which was statistically significant at doses of 1130 and 1600 kU/kg body weight (FIG. 5).

5. Overall Assessment

In the described model for coronary artery thrombosis in dogs, the protein described supra proved to be a thrombolytic agent which achieved a 100% rate of reperfusion without major influence on fibrinogen concentration, and without significant increase in the bleeding time. It was clearly superior (factor of 11.5) in its thrombolytic potency after an intravenous bolus injection in comparison with wt-tPA. Furthermore, the investigation of the pharmacokinetic profile of the protein revealed that, in comparison with wt-tPA, the clearance of the invention was reduced, nine-fold.

EXAMPLE 5

The present pharmacological study was performed to characterize pharmacokinetic, pharmacodynamic, and safety parameters of a second thrombolytically active protein, i.e., K1K2P. The thrombolytically active protein K1K2P consists of the kringle 1 (K1), the kringle 2 (K2), and the protease domains of human t-PA but lacks the finger and the epidermal growth factor domains. The amino acid sequence corresponds to amino acids 1-5 and 86-527 of Pennica et al., supra. K1K2P is not glycosylated because it is produced by recombinant DNA technology in *E coli* cells. K1K2P has a specific activity of 6500,000±200,000 U/mg.

1) Pharmacokinetics and Pharmacodynamics of K1K2P in Rabbits

New Zealand white rabbits were used to investigate thrombolytic and pharmacokinetic properties of K1K2P as compared to recombinantly produced, wild type t-PA or ("wt-tPA") after intravenous administration via the marginal ear vein. The plasma concentration of activity of the protein was measured by a plasminogenolytic assay as described by Verheijen et al. (Thromb Haemostas 1982, 48: 266–269) incorporated by reference herein. Briefly, 9 parts of blood were drawn on 1 part citrate (final concentration: 11 mM) for preparation of plasma samples which were stored, deep frozen, until assayed. Inhibitors were removed from the thawed plasma by preparation of euglobulin fractions using well known techniques. Plasminogenolytic activity was measured by an indirect spectrophotometric method. CNBr cleavage products of human fibrinogen were used for stimulation of the thrombolytically active protein to activate Glu plasminogen added to the sample, in order to form plasmin, which, in turn, reacted with the synthetic plasmin substrate Tos-Gly-Pro-Lys-4-NA (CHROMOZYM™PL, Boehringer Mannheim, Mannhelm Germany) (a chromogenic substrate). A t-PA standard, calibrated using the international standard for t-PA, batch 83/517 from the National Institute for Biological Standards and Control (Holly Hill, Hampstead, London, UK) was used as the standard for determining the activity of the thrombolytically active proteins described herein.

Non-linear regression was used to calculate pharmacokinetic parameters. The parameters were calculated individually using a bi-exponential pharmacokinetic model.

K1K2P has a 7.6-fold longer dominant half life than alteplase (15.1±3 min vs. 2.0±0.01 min) (Table 6). The total plasma clearance rate of K1K2P is 4.1-fold lower than that of alteplase and the area under the curve (AUC) of K1K2P is 4.2-fold higher than that of alteplase in rabbits (see Table 6).

EXAMPLE 6

In further experiments, the jugular vein thrombosis model was used as described by D. Collen (J. Clin. Invest. 71, 368, 1983). Briefly, a radiolabelled clot was produced in the jugular vein and the disappearance of radioactivity from the clot was used for calculation of the rate of thrombolysis (percentage of initial clot). Blood samples were taken on citrate, as in example 5, supra to measure plasma fibrinogen by a clotting rate method according to Clauss, supra. K1K2P or wt-tPA (specific activity=800,000 IU/mg) was administered intravenously via the ear vein contralaterally to the jugular vein thrombus.

K1K2P achieved a rate of 50% thrombolysis at a dose of 200 kU/kg (Table 7), whereas a dose of 1153 kU/kg of wt-tPA was calculated by linear regression analysis to be the effective dose which produces 50% thrombolysis ($ED_{50}$). Therefore, the thrombolytic potency of K1K2P is 5.8-fold higher than that of wt-tPA i.e., a 5.8-fold lower dose of K1K2P than that of wt-tPA is sufficient to achieve the same rate of 50% thrombolysis. Residual fibrinogen was not significantly reduced by K1K2P.

EXAMPLE 7

The canine model of coronary arterial thrombosis as described in Example 7 was used to examine efficacy, pharmacokinetics and safety of K1K2P in vivo. Briefly, six adult beagle dogs were anesthetized, catheterized and surgically prepared in order to produce a left circumflex coronary artery thrombus by electrolytic injury. K1K2P was administered as a single i.v. bolus injection of 200 kU/kg (=0.325 mg/kg) over 1 min. into heparinized dogs. Blood flow was followed for 2 hours post injection of K1K2P. Plasma samples (final citrate concentration: 11 mM) were taken before and repeatedly after administration of K1K2P in order to measure plasma concentration of functionally active K1K2P and hemostasis parameters (fibrinogen, plasminogen, $\alpha_2$-antiplasmin). The K1K2P functional assay and the coagulation assays were performed as described in Example 7 by a clotting rate or a chromogenic method. Thrombolysis parameters were as follows: the incidence of reperfusion, the time to reperfusion, the incidence of reocclusion, the residual thrombus wet weight.

The main pharmacokinetic parameters of K1K2P are summarized in Table 6 in comparison with alteplase. K1K2P had a 6.7-fold longer dominant half life (10.7 min) than wt-tPA at identical doses (200 kU/kg). The total plasma clearance rate (7.6 ml/min/kg) was 5.5-fold lower than that of wt-tPA. Accordingly, the area under the curve (AUC; 458 IU h/ml) was 5.4-fold higher than that of wt-tPA.

The thrombolysis and hemostatic results are summarized in Table 8. K1K2P achieved a 50% reperfusion rate at 35±12 min. post injection. The effective dose of 50% reperfusion rate after K1K2P (=200 kU/kg) was 4.8-fold lower than that of alteplase ($ED_{50}$=961 kU/kg), i.e., a 4.8-fold lower dose of K1K2P compared with alteplase is sufficient to achieve the same rate of 50% reperfusion indicating a 4.8-fold higher thrombolytic potency of K1K2P.

The residual thrombus wet weight (5.7±1.2 mg) was lower than that of the placebo control group (9.6±1.2 mg, see Example 7). Residual fibrinogen (Table 8) was not significantly reduced. Bleeding time (Table 9) was slightly, but not significantly prolonged (maximum prolongation compared with baseline: 1.2-fold) in contrast to wt-tPA (max. prolongation: more than 2-fold, see Example 7).

The following summarizes the properties of K1K2P as ascertained by examples 5–7.

1) Pharmacokinetics: The half life of K1K2P is species-dependent and is 6.7–7.6-fold longer than that of wild type t-PA. The clearance rate of K1K2P is species-dependent and is 4.1–5.5-fold higher than that of wild type t-PA. The area under the curve is 4.2–5.5-fold higher than that of wt-tPA.
2) Pharmacodynamics: The effective dose which induces a 50% thrombolysis rate ($ED_{50}$) of K1K2P is species-dependent and is 4.8–5.8-fold lower than that of wt-tPA, indicating a 4.8–5.8-fold higher thrombolytic potency compared with the wild type molecule.
3) Safety: The bleeding time after K1K2P administration is not significantly prolonged (max. prolongation: 1.2-fold) in contrast to wild type t-PA (more than 2-fold). Residual fibrinogen after K1K2P injection is not significantly reduced in contrast to that after wild type t-PA administration (below 25%).

TABLE 6

Pharmacokinetic Parameters of K1K2P and of Alteplase Derived from Computer Calculations of the Plasma Concentration Time Data Based on t-PA Activity

| Thrombo-lytically active protein | Rabbit | | Dog | |
|---|---|---|---|---|
| | Alteplase | K1K2P | Alteplase | K1K2P |
| Dose (kU/kg) | 400 | 200 | 200 | 200 |
| N | 6 | 6 | 6 | 6 |
| Dominant half life (min) | 2.0 ± 0.01 | 15.1 ± 3.0 | 1.6 ± 0.2 | 10.7 ± 1.5 |
| Total plasma clearance (ml/min/kg) | 26.1 ± 6.0 | 6.3 ± 1.5 | 41.8 ± 11.4 | 7.6 ± 1.8 |
| AUC (IU · h/ml) | 266 ± 55 = 133 (at 200 ku/kg)* | 556 ± 119 | 84 ± 24 | 458 ± 101 |

Mean ± SD;
AUC, area under the curve;
*since AUC is dose-dependent a dose-correction by a factor of 2 (400:2 = 200) had to be done to make the results comparable a the same dose.

TABLE 7

Rate of thrombolysis and residual fibrinogen

| Thrombolytically active protein | Dose (kU/kg) | N | Rate of thrombolysis (%) | Residual fibrinogen (% of the initial value) |
|---|---|---|---|---|
| Solvent | — | 6 | 12.9 ± 0.9 | 89.5 ± 2.1 |
| K1K2P | 200 | 6 | 50.7 ± 6.5 | 81.1 ± 5.1 |
| Alteplase | 200 | 6 | 24.1 ± 3.7 | 90.5 ± 2.6 |
| Alteplase | 800 | 6 | 44.6 ± 4.8 | 81.4 ± 3.4 |

Mean ± SEM; residual fibrinogen was determined at termination of the experiment.

TABLE 8

Thrombolysis and Hemostasis Parameters of K1K2P in the Canine Model or Coronary Artery Thrombosis

| Parameter | K1K2P | Placebo Control |
|---|---|---|
| Dose (kU/kg) | 200 | — |
| Incidence of reperfusion (%) | 3/6 (=50%) | 0/6 |
| $ED_{50}$ (kU/kg) | 200 | — |
| Time to reperfusion (min) | 35 ± 12 | — |
| Incidence of reocclusion | 2/3 | — |
| Residual thrombus wet weight (mg) | 57 + 12 | 96 ± 12 |
| Residual fibrinogen (% of baseline) | 95 ± 6 | 106 ± 2 |
| Residual plasminogen (% of baseline) | 89 ± 3 | 103 |
| Residual $\alpha_2$-antiplasmin (% of baseline) | 67 ± 3 | 92 ± 11 |
| Residual platelet count (% of baseline) | 104 ± 5 | 101 ± 3 |

Mean ± SEM; n = 6;
$ED_{50}$, effective dose which induced a 50% reperfusion rate; residual hemostasis parameters were determined at termination of the experiments (at 2 h post injection).

TABLE 9

| Bleeding Time in Dogs before and after i.v. Injection of 200 kU/kg K1K2P | |
|---|---|
| Time Point (min) | Bleeding Time (min) |
| 0 | 2.3 ± 0.2 |
| 10 | 2.8 ± 0.2 |
| 30 | 2.8 ± 0.3 |
| 60 | 2.6 ± 0.2 |
| 90 | 2.5 ± 0.1 |
| 120 | 2.5 ± 0.3 |

Mean ± SEM; n = 6.

The foregoing examples, which involve the thrombolytically active proteins K2P and K1K2P, show the unexpected superiority of these molecules as compared to wild type t-PA. Both molecules share the properties listed supra, i.e., regarding pharmacodynamics, pharmacokinetics, and safety profiles.

Thus, the invention in its broadest aspect, is the treatment of subjects in need of thromboembolic therapy, i.e., those suffering from a thromboembolic condition, via administering to the subject an amount of a thrombolytically active protein which has all of the following properties: i) a pharmacokinetic profile which is from 4.5 to 9.5 times greater than that of wild type t-PA; ii) a pharmacodynamic profile which is 4.0 to 11.5 times greater than wild type t-PA, and ii) which has a safety profile which is about 2 times that of wild type t-PA. The amount of the protein so administered should be sufficient to lyse thrombi in the subject. This amount will differ, of course, from subject to subject, based upon the subject's size, weight, health, and so forth, as well as the activity profile of the protein administered. As described herein, however, these are factors which the skilled artisan is accustomed to dealing with on a regular basis. "Wild type t-PA" as used herein refers to the t-PA molecule described by Pennica et al., supra, as well as Collen et al., U.S. Pat. No. 4,666,075, the disclosures of which are both incorporated by reference in their entirety.

The preferred thrombolytically active proteins are K2P and K1K2P, as described supra. These proteins consist of amino acids 1–3 and 1760527 (K2P) and amino acids 1–5 and 86–527 (K1K2P) of wild type t-PA, respectively. Other thrombolytically active proteins which fulfill the listed criteria may also be used.

It was noted, supra, that the pharmacokinetic and pharmacodynamic properties were species dependent. What these means is that certain properties, such has half life, can change from animal to animal; however, all values are within the recited ranges of the claimed invention.

"Area Under the Curve", or "AUC" referred to supra, is a well known property in the thrombolytic art. It refers to an accepted mathematical model where half life and clearance values are fitted, mathematically, to a standard calculation system.

Finally, in considering the safety profile, baseline values refer to the bleeding time (i.e., the time from onset of bleeding caused by incision to the halt of this bleeding) of the particular subject animal prior to treatment. Plasmafibrinogen levels, as used herein, refer to the values before treatment (pretreatment or normal levels), and posttreatment levels.

As indicated, supra, two preferred embodiments of the invention relate to the use of K2P and K1K2P. In other preferred embodiments, the thrombolytically active protein is one which has an average half life 4½–5 times longer than that of wt-tPA. The half life can actually range from 3–8 times longer than that of the reference molecule, i.e., wt-tPA. In additional preferred embodiments, the pharmacokinetic profile is one where average clearance rate is from 3–16 times less than that of wt-tPA, most preferably 3–8 times less than this reference. The area under the curve is preferably 3–18 times that of wt-tPA, and most preferably 8–9.5 times the reference value.

The pharmacodynamic profile of the molecules used in the invention is one where the effective dose of the thrombolytically active protein is one that is 4–11.5 times lower than that of wt-tPA, "effective dose" being the $ED_{50}$ value explained supra. More preferably, the thrombolytically active proteins are those which have a reperfusion time of from 9–44 minutes, most preferably 15–31 minutes. In additional preferred embodiments, the thrombolytically active proteins are those which do not prolong bleeding time more than twice that of wt-tPA.

Other features which flow from the invention will be clear to the artisan and need not be repeated here.

It will be understood that the specification and examples are illustrative but not limitative of the present invention and that other embodiments within the spirit and scope of the invention will suggest themselves to those skilled in the art.

---

We claim:

1. Method for treating a thromboembolic condition comprising administering to a subject in need thereof an amount of a thrombolytically active protein selected from the group consisting of (a) the protein consisting of the amino acid sequence set forth in SEQ ID NO: 1, and (b) the protein consisting of amino acids 1–5 and 86–527 of wild type t-PA, wherein said thrombolytically active protein i) has a pharmakokinetic profile 4.5–9.5 times greater than that of wild type t-PA,
   ii) has a pharmacodynamic profile 4.0–11.5 times greater than that of wild type t-PA, and
   iii) prolongs bleeding time no more than about two times base line bleeding time, sufficient to lyse thrombi in said subject.

2. Method according to claim 1 wherein the pharmacokinetic profile is characterized by a half life about 3–8 times greater than that of wild type t-PA.

3. Method according to claim 2 wherein the pharmacokinetic profile is characterized by an average half-life 4.5–5 times that of wild type-tPA.

4. Method according to claim 3 wherein the pharmacokinetic profile is characterized by an average clearance rate of about 3–16 times less than that of wild type t-PA.

5. Method according to claim 1 wherein the pharmacokinetic profile is characterized by an average clearance rate 6.9–9.0 times less than that of wild type t-PA.

6. Method of claim 5 wherein the area under the curve is 3–18 times greater than that of wild type t-PA.

7. Method according to claim 1 wherein the pharmacokinetic profile is characterized by an average area under the curve 8.0–9.5 times greater than that of wild type t-PA.

8. Method according to claim 1 wherein the pharmacodynamic profile is characterized by an effective dose about 4.0–11.5 times less than that of wild type t-PA.

9. Method according to claim 1 wherein the pharmacodynamic profile of said thrombolytically active protein is characterized by an average reperfusion time of 9–44 minutes.

10. Method according to claim 9 wherein the reperfusion time is 15–31 minutes.

11. Method of claim 1, wherein said thrombolytically active protein consists of the amino acid sequence set forth in SEQ ID NO: 1.

12. Method of claim 1, wherein said thrombolytically active protein consists of amino acids 1–5 and 86–527 of wild type t-PA.

13. Method of claim 1, wherein said thromboembolic condition is acute myocardial infarction.

14. Method of claim 1, wherein said thromboembolic condition is a pulmonary embolism.

15. Method of claim 1, wherein said throboembolic condition is a stroke.

* * * * *

UNITED STATES PATENT AND TRADEMARK OFFICE
CERTIFICATE OF CORRECTION

PATENT NO. : 5,676,947
DATED : October 14, 1997
INVENTOR(S) : Martin, et al.

It is certified that error appears in the above-indentified patent and that said Letters Patent is hereby corrected as shown below:

In cover page, in the section titled Related U.S. Application Data, line [60], change serial number "968.171" to - - 986.171 - -.
In cover page, in the section titled Other Publications, line [2], change "613" to - - 63 - -.
In cover page, in the section titled Other Publications, line [2], insert "(1990)" at end of sentence.
In cover page, in the section titled Other Publications, line [2], insert "Novel Recombinant Tissue Plasminogen Activators Produced in Escherichia Coli" before "Ann. N.Y. Acad. Sci."
In cover page, in the section titled Other Publications, line [3], change "Thromb & Haernost." to - - Novel Tissue Plasminogen Activatory Produced in E. coli and Their Properties Thromb & Haernost - -.
In cover page, in the section titled Other Publications, line [3], change "393 1989" to - - 393 Abstract 1241 1989 - -.

In column 8, line 50, change "radiolabelled" to - - radiolabeled - -.

UNITED STATES PATENT AND TRADEMARK OFFICE
CERTIFICATE OF CORRECTION

PATENT NO. : 5,676,947
DATED : October 14, 1997
INVENTOR(S) : Martin, et al.

It is certified that error appears in the above-identified patent and that said Letters Patent is hereby corrected as shown below:

In column 10, line 26, change "comparable a" to - - comparable at - -.

In column 12, line 3, change "these" to - - this - -.

Signed and Sealed this

Eighth Day of May, 2001

Attest:

NICHOLAS P. GODICI

Attesting Officer      Acting Director of the United States Patent and Trademark Office

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 355 amino acids
        ( B ) TYPE: amino acids
        ( C ) TOPOLOGY: linear ( x i ) SEQUENCE DESCRIPTION: SEQ ID NO: 1:

```
Ser  Tyr  Gln  Gly  Asn  Ser  Asp  Cys  Tyr  Phe  Gly  Asn  Gly  Ser  Ala  Tyr
                    5                        10                       15
Arg  Gly  Thr  His  Ser  Leu  Thr  Glu  Ser  Gly  Ala  Ser  Cys  Leu  Pro  Trp
                   20                        25                       30
```

```
Asn Ser Met Ile Leu Ile Gly Lys Val Tyr Thr Ala Gln Asn Pro Ser
        35              40              45
Ala Gln Ala Leu Gly Leu Gly Lys His Asn Tyr Cys Arg Asn Pro Asp
    50              55                  60
Gly Asp Ala Lys Pro Trp Cys His Val Leu Lys Asn Arg Arg Leu Thr
65              70                  75                      80
Trp Glu Tyr Cys Asp Val Pro Ser Cys Ser Thr Cys Gly Leu Arg Gln
            85                  90                  95
Tyr Ser Gln Pro Gln Phe Arg Ile Lys Gly Gly Leu Phe Ala Asp Ile
            100             105                 110
Ala Ser His Pro Trp Gln Ala Ala Ile Phe Ala Lys His Arg Arg Ser
        115             120                 125
Pro Gly Glu Arg Phe Leu Cys Gly Gly Ile Leu Ile Ser Ser Cys Trp
    130             135                 140
Ile Leu Ser Ala Ala His Cys Phe Gln Glu Arg Phe Pro Pro His His
145             150                 155                     160
Leu Thr Val Ile Leu Gly Arg Thr Tyr Arg Val Val Pro Gly Glu Glu
            165                 170                 175
Glu Gln Lys Phe Glu Val Glu Lys Tyr Ile Val His Lys Glu Phe Asp
        180                 185                 190
Asp Asp Thr Tyr Asp Asn Asp Ile Ala Leu Leu Gln Leu Lys Ser Asp
    195                 200                 205
Ser Ser Arg Cys Ala Gln Glu Ser Ser Val Val Arg Thr Val Cys Leu
    210             215                 220
Pro Pro Ala Asp Leu Gln Leu Pro Asp Trp Thr Glu Cys Glu Leu Ser
225             230                 235                     240
Gly Tyr Gly Lys His Glu Ala Leu Ser Pro Phe Tyr Ser Glu Arg Leu
            245                 250                 255
Lys Glu Ala His Val Arg Leu Tyr Pro Ser Ser Arg Cys Thr Ser Gln
            260             265                 270
His Leu Leu Asn Arg Thr Val Thr Asp Asn Met Leu Cys Ala Gly Asp
        275             280                 285
Thr Arg Ser Gly Gly Pro Gln Ala Asn Leu His Asp Ala Cys Gln Gly
    290             295                 300
Asp Ser Gly Gly Pro Leu Val Cys Leu Asn Asp Gly Arg Met Thr Leu
305             310                 315                     320
Val Gly Ile Ile Ser Trp Gly Leu Gly Cys Gly Gln Lys Asp Val Pro
            325                 330                 335
Gly Val Tyr Thr Lys Val Thr Asn Tyr Leu Asp Trp Ile Arg Asp Asn
            340             345                 350
Met Arg Pro
        355
```